United States Patent
Min et al.

(10) Patent No.: US 9,301,954 B2
(45) Date of Patent: Apr. 5, 2016

(54) PHARMACEUTICAL COMPOSITION FOR THE PREVENTION OR TREATMENT OF OSTEOARTHRITIS CONTAINING REBAMIPIDE AS AN ACTIVE INGREDIENT

(75) Inventors: Jun-Ki Min, Gyeonggi-do (KR); Mi-La Cho, Seoul (KR); Yun-Ju Woo, Seoul (KR); Hye-Jwa Oh, Seoul (KR); Young-Ok Jung, Seoul (KR); Geun-Hyeog Lee, Gyeonggi-do (KR); Byong-Sun Choi, Seoul (KR); Jin-Ha Park, Gyeonggi-do (KR); Eun-Young Kwak, Seoul (KR)

(73) Assignees: HANLIM PHARMACEUTICAL CO., LTD, Gyeonggi-Do (KR); CATHOLIC UNIVERSITY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 13/582,929

(22) PCT Filed: Mar. 4, 2011

(86) PCT No.: PCT/KR2011/001497
§ 371 (c)(1),
(2), (4) Date: Sep. 5, 2012

(87) PCT Pub. No.: WO2011/108882
PCT Pub. Date: Sep. 9, 2011

(65) Prior Publication Data
US 2013/0065920 A1    Mar. 14, 2013

(30) Foreign Application Priority Data
Mar. 5, 2010   (KR) .................... 10-2010-0019671

(51) Int. Cl.
| | | |
|---|---|---|
| *A01N 43/42* | (2006.01) | |
| *A61K 31/47* | (2006.01) | |
| *A61K 31/4704* | (2006.01) | |
| *A61K 9/20* | (2006.01) | |

(52) U.S. Cl.
CPC ........... *A61K 31/4704* (2013.01); *A61K 9/2004* (2013.01)

(58) Field of Classification Search
USPC ........................................................ 514/312
See application file for complete search history.

(56) References Cited

U.S. PATENT DOCUMENTS

| | | | |
|---|---|---|---|
| 6,900,026 B2 * | 5/2005 | Wallace et al. ................ 435/18 |
| 2004/0157928 A1 * | 8/2004 | Kim et al. ..................... 514/570 |
| 2004/0175422 A1 * | 9/2004 | Tomohira ...................... 424/468 |
| 2005/0113392 A1 * | 5/2005 | Clark et al. ................... 514/256 |
| 2012/0172394 A1 * | 7/2012 | Min et al. ..................... 514/312 |

OTHER PUBLICATIONS

Wantanabe, T.; Higuchi, K.; Hamaguchi, M.; Tanigawa, T.; Wada, R.; Tominaga, K.; Fujiwara, Y.; Arakawa, T. Rebamipide Prevents Delay of Acetic Acid-Induced Gastric Ulcer Healing Caused by Helicobacter pylori Infection in Mongolian Gerbils, Jul. 2002, Digestive Diseases and Sciences, vol. 47, pp. 1582-1589.*
Kohashi, M.; Ishimaru, N.; Arakaki, R.; Hayashi, Y. Effective Treatment With Oral Administration of Rebamipide in a Mouse Model of Sjogren's Syndrome, Feb. 2008, Arthritis & Rheumatism, vol. 58, pp. 389-400.*
Arakawa, T.; Higuchi, K.; Fujiwara, Y.; Watanabe, T.; Tominaga, K.; Sasaki, E.; Oshitani, N.; Yoshikawa, T.; Tarnawski, A. S.; 15th Anniversary of Rebamipide: Looking Ahead to the New Mechanisms and New Applications, Oct. 2005, Digestive Diseases and Sciences, vol. 50, pp. S3-S11.*
Namazi, Fasudil: A potential addition to the anti-arthritis weaponry, 2007, Medical Hypotheses, 1425.*
Park et al. (J. Clin. Biochem. Nutr. 2007, 40, 148-155).*
Cho et al. (Clin. Ther., 2009, 11, 2712-21).*
Kohashi, Masayuki et al., "Effective treatment with oral administration of rebamipide in a mouse model of sjogrens' syndrome". Arthritis & Rheumatism, vol. 58, No. 2, pp. 389-400 (2008).
International Search Report for PCT/KR2011/001497 dated Apr. 3, 2011.
Tokuhara, et al., "Rebamipide, anti-gastric ulcer drug, up-regulates the induction of iNOS in proinflammatory cytokine-stimulated hepatocytes", Nitric Oxide, vol. 18, pp. 28-36, (2008).
A EPO Notice of Intention to Grant to equivalent EP application, for EP Application No. 11 750 939.8, 21 pages, dated Feb. 13, 2014.

* cited by examiner

*Primary Examiner* — Dennis Heyer
*Assistant Examiner* — Daniel M Podgorski
(74) *Attorney, Agent, or Firm* — Vorys, Sater, Seymour & Pease LLP; Mih Suhn Koh

(57) ABSTRACT

The present invention provides a method for preventing or treating osteoarthritis comprising administrating rebamipide or a pharmaceutical composition comprising rebamipide as an active ingredient and a pharmaceutically acceptable carrier to a subject in need thereof. The pharmaceutical composition may be for oral administration, for example an oral solid dosage form of a tablet or capsule form. The pharmaceutical composition may be formulated into a unit dosage form suitable for orally administering rebamipide in a dose ranging from 0.5 to 50 mg/kg, preferably from 0.6 to 6 mg/kg.

3 Claims, 3 Drawing Sheets

PHARMACEUTICAL COMPOSITION FOR THE PREVENTION OR TREATMENT OF OSTEOARTHRITIS CONTAINING REBAMIPIDE AS AN ACTIVE INGREDIENT

This is a National Phase Application filed under 35 U.S.C. §371 as a national stage of PCT/KR2011/001497, filed on March 4, an application claiming the benefit under 35 U.S.C. §119 of Korean Application No. 10-2010-0019671, filed on Mar. 5, 2010 the content of each of which is hereby incorporated by reference in their entirety.

TECHNICAL FIELD

The present invention relates to a method for preventing or treating osteoarthritis.

BACKGROUND ART

Osteoarthritis, one of the types of arthritis, is also referred to as degenerative arthritis. It is said that osteoarthritis is an arthritis caused by degenerative changes in the cartilage and adjacent bone in the synovial joints. That is, osteoarthritis is characterized by gradual loss of articular cartilage, combined with thickening of the subchondral bone, bony outgrowths at the joint margins, and nonspecific synovial inflammation. Osteoarthritis is caused by cartilage damages according to aging and/or physical stresses (for example, obesity, trauma, etc.). Therefore, osteoarthritis involves severe pain and/or movement disorder in the weight-bearing joints, such as knee joint and hip joint; and the negligence thereof for long time results in joint malformations.

Typically, osteoarthritis is progressed in the following steps: the cartilage change phase in which edema occurs by the increase of water contents in the cartilage (step 1); the fibrillation phase in which the cartilage is destructed, thereby resulting in erosion of the cartilage surface, bone exposure, and narrow articular cavity (step 2); the overall cartilage reduction phase in which, although chondrocytes initiate compensatory cartilage formation, cartilage breakdown occurs faster than cartilage formation (step 3); the bone malformation phase in which the bone modification results in joint malformations and dysfunctions (step 4); and the changes of articular soft tissue in which the soft tissue become thickened (step 5).

Rheumatoid arthritis, which belongs to a different type of arthritis from osteoarthritis, is a chronic autoimmune disease characterized by inflammation and proliferation of synovial cells; and causes osteoporosis and bone erosion around in the joints, unlike osteoarthritis. Typically, rheumatoid arthritis is progressed in the following steps: inflammation in the synovial membrane spreads to joint capsules, ligaments, tendons, etc (step 1); progressive destruction of joint cartilage leads to narrowing the joint space and destroying tension of both joint capsule and ligament (step 2); inflammation infiltrates into bone, thereby inducing partial bone erosion (step 3); and functional disability is caused in the joint (step 4). Therefore, rheumatoid arthritis and osteoarthritis are quite different in their etiologies and progressions, and therefore the therapeutic methods thereof are also different.

The treatment of osteoarthritis used in the prior arts includes the use of therapeutic agents, for example acetaminophen, tramadol, nonsteroidal antiinflammatory drugs (NSAIDs), diacerin, glucosamine, etc. Among them, the NSAIDs have been reported to induce side effects in the gastrointestinal tract, such as gastric ulcer, duodenal ulcer, etc. Therefore, when these drugs are applied to a patient suffering from osteoarthritis and potential problem of gastrointestinal side effects, a cytoprotective agent (e.g., rebamipide, etc), a H2-receptor antagonist (e.g., cimetidine, ranitidine, etc), and/or a proton pump inhibitor (e.g., omeprazole) are also co-administered.

DETAILED DESCRIPTION OF THE INVENTION

Technical Problem

The present inventors unexpectedly found, during the treatment of various patients suffering from osteoarthritis in the clinics, that rebamipide per se co-administered for avoiding gastrointestinal side effects has an activity for preventing or treating osteoarthritis. It is very surprising since it has not been reported that rebamipide could be related to improvement and/or therapeutic effect against osteoarthritis.

Therefore, the present invention provides a method for preventing or treating osteoarthritis comprising administrating rebamipide as an active ingredient to a subject in need thereof.

Technical Solution

According to an aspect of the present invention, there is provided a method for preventing or treating osteoarthritis comprising administering rebamipide or a pharmaceutical composition comprising rebamipide as an active ingredient and a pharmaceutically acceptable carrier to a subject in need thereof.

The pharmaceutical composition may be for oral administration, for example an oral solid dosage form of a tablet or capsule form. The pharmaceutical composition may be formulated into a unit dosage form suitable for orally administering rebamipide in a dose ranging from 0.5 to 50 mg/kg, preferably from 0.6 to 6 mg/kg.

Advantageous Effects

It is newly found by the present invention that rebamipide has an activity for preventing or treating osteoarthritis. Therefore, the pharmaceutical composition comprising rebamipide may be used for preventing or treating osteoarthritis, independently or in combination of other therapeutic agent(s) for treating osteoarthritis.

BEST MODE FOR CARRYING OUT THE INVENTION

Figure 1:
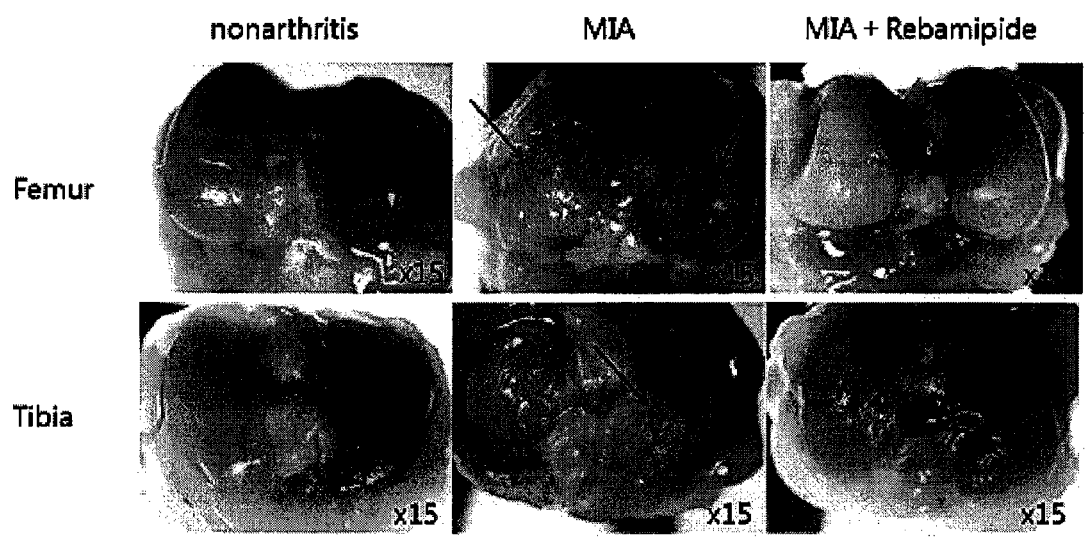
FIG. 1 is the results obtained by observing the femurs and tibias isolated from the rats under a microscope at the 7th day after the osteoarthritis induction.

As used herein, the term "rebamipide" includes all forms of rebamipide, such as anhydrous form, hydrate form (e.g., hemihyrate form), crystalline forms, etc; and a pharmaceutically acceptable salt thereof. The pharmaceutically acceptable salt includes an inorganic ionic salt originated from for example calcium, potassium, sodium, and magnesium; an inorganic acid salt originated from for example hydrochloric acid, nitric acid, phosphoric acid, hydrobromic acid, hydroiodic acid, and sulfuric acid; an organic acid salt originated from for example acetic acid, formic acid, succinic acid, tartaric acid, citric acid, trichloroacetic acid, trifluoroacetic acid, gluconic acid, benzoic acid, lactic acid, fumaric acid, and maleic acid; an sulfonic acid salt originated from for example methanesulfonic acid, ethanesulfonic acid, benzenesulfonic acid, p-toluenesulfonic acid, and naphthalenesulfonic acid; an amino acid salt originated from for example glycine, arginine, and lysine; and an amine salt originated from for example trimethylamine, triethylamine, ammonia, pyridine, and picoline.

The present invention provides a method for preventing or treating osteoarthritis comprising administrating rebamipide or a pharmaceutical composition comprising rebamipide as an active ingredient and a pharmaceutically acceptable carrier to a subject in need thereof.

As described in the Example below, when osteoarthritis was induced in rats by administering monosodium iodoacetate (MIA) known as an osteoarthritis-inducing agent and then rebamipide was orally administered to the rats, the cartilage damages were significantly inhibited (see FIG. 1). As a result of histological analyses, when rebamipide was orally administered, the losses of cartilage and its components were similar to those of the normal rats; and the cartilage destruction and the degradation of its components were favorably changed (see FIG. 2 and FIG. 3). These results show that the rebamipide used as a cytoprotective agent has an excellent activity for treating osteoarthritis.

The pharmaceutical composition of includes a pharmaceutically acceptable carrier, and can be formulated according to conventional methods into oral dosage forms such as powders, granules, tablets, capsules, suspensions, emulsions, syrups, or aerosols; external dosage forms; suppository; or sterile injection solution. Preferably, the pharmaceutical composition of the present invention may be a form for oral administration, for example an oral solid dosage form of a tablet or capsule form. For example, the pharmaceutical composition of the present invention may in the form of a commercially marketed rebamipide-containing tablet (for example, "Mucosta™ Tablet", Otsuka Pharmaceutical Co., Ltd.). The pharmaceutically acceptable carrier includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, hydroxypropyl cellulose, low-substituted hydroxypropyl cellulose, hydroxypropyl methylcellulose 2910, polyethylene glycol 6000, polyvinylpyrrolidone, methyl hydroxybenzoate, propyl hydroxybenzoate, titanium dioxide, talc, magnesium stearate, and mineral oil, but not limited thereto. The pharmaceutical composition may further include a dilluent or an excipient, such as filler, expander, binder, humectant, disintegrant, or surfactant. A solid oral formulation includes for example a tablet, a pill, a powder, a granule, or a capsule. Such solid formulations may include at least one excipient selected from, for example, starch, calcium carbonate, sucrose, lactose, and gelatin. In addition, such solid formulations may further include a lubricant, such as magnesium stearate or talc. Specifically, the pharmaceutical composition of the present invention may be a tablet form comprising rebamipide as an active ingredient; and low-substituted hydroxypropyl cellulose, microcrystalline cellulose, titanium dioxide, hydroxypropyl methylcellulose 2910, polyethylene glycol 6000, hydroxypropyl cellulose, and magnesium stearate as a carrier. A liquid oral formulation includes a suspension, a solution, an emulsion, or syrup. In addition, the liquid oral formulation may include a dilluent such as water, liquid paraffin; a humectant; a sweetening agent; an odorant; or a preservative. A parenteral formulation includes a sterile aqueous solution, a non-aqueous solution, a suspension, an emulsion, a lyophilized formulation, or a suppository. Non-aqueous solvents or suspending agents includes propylene glycol, polyethylene glycol, vegetable oil such as olive oil, or injectable esters such as ethyl oleate. Bases for suppository may be witepsol, macrogol, Tween 61, cacao butter, Laurin, or glycerogelatine.

In the pharmaceutical composition according to the present invention, a dose of rebamipide may vary depending on patient's state or body weight, seriousness of disease, dosage forms, administration routes, and the period of administration, and can be appropriately determined by a person having ordinary skill in the art. For example, rebamipide may be administered in a dose of 0.1 to 100 mg/kg, preferably 0.5 to 50 mg/kg, more preferably 0.6 to 6 mg/kg, per day. Therefore, the pharmaceutical composition may be formulated into a unit dosage form suitable for orally administering rebamipide in a dose ranging from 0.5 to 50 mg/kg, preferably from 0.6 to 6 mg/kg. The administration can be completed once or through several times per day. The pharmaceutical composition of the present invention can be also administered independently or in combination with other therapeutic agent(s) for osteoarthritis such as non-steroidal anti-inflammatory drugs (NSAIDs), etc. When administered as a combination, the therapeutic agent(s) can be administered sequentially or at the same time.

Hereinafter, the present invention will be described more specifically by the following working example. However, the following working example is provided only for illustrations and thus the present invention is not limited to or by it.

EXAMPLE

Evaluation of Therapeutic Efficacy of Rebamipide on Osteoarthritis According to Oral Administration (1) Test Method About 5 week old male Wistar rats were used. Monosodium iodoacetate (MIA) was dissolved in a physiological saline; and then administered to the rats in the dose of 4 mg/50 μl via the right knee thereof, so as to induce osteoarthritis.

The rats were divided into 3 groups, each having 5 rats. The first group (non-arthritis) was a non-treated group, i.e., a normal control group. The second group (MIA) was an osteoarthritis-induced group through the MIA administration. The rats of the third group (MIA+Rebamipide) were administered with the MIA to induce osteoarthritis; and then orally administered with rebamipide every day for 7 days.

At the 7th day after the MIA induction, the femurs and the tibias were isolated from the rats of each group and then observed under a dissecting microscope. After H&E staining, the knee joint sites were observed through a low-magnification lens. In the results, the nucleus is shown in blue-violet color and the cytoplasm is shown in pink color. After completion of the stainings, the tissues were observed in detail, dividing two sites, i.e., the upper site of the knee (shown as "F" which is the abbreviation of femurs) and the lower site of the knee (shown as "T" which is the abbreviation of tibias). The knee joints were stained with Safranin O, which can show losses of the cartilage proteoglycans. The tartrate-resistant acid phosphatase (TRAP) staining for osteoclasts, was performed at 37° C. for 30 minutes, using a leukocyte acid phosphatase kit (Sigma 387-A, USA). The TRAP-positive cells were shown in red-violet color. The multinucleated cells (having above 3 nuclei) were considered as TRAP-positive cells (osteoclasts), which were counted under an optical microscope.

(2) Test Results

As a result of the observation of the femurs and tibias isolated from the rats of each group under a dissecting microscope at the 7th day after the MIA induction, the group not administered with rebamipide showed damages in the cartilage sites (see the red arrows of the middle pictures in FIG. 1). However, the group orally administered with rebamipide showed little damages in the cartilage sites (see FIG. 1).

Figure 2:
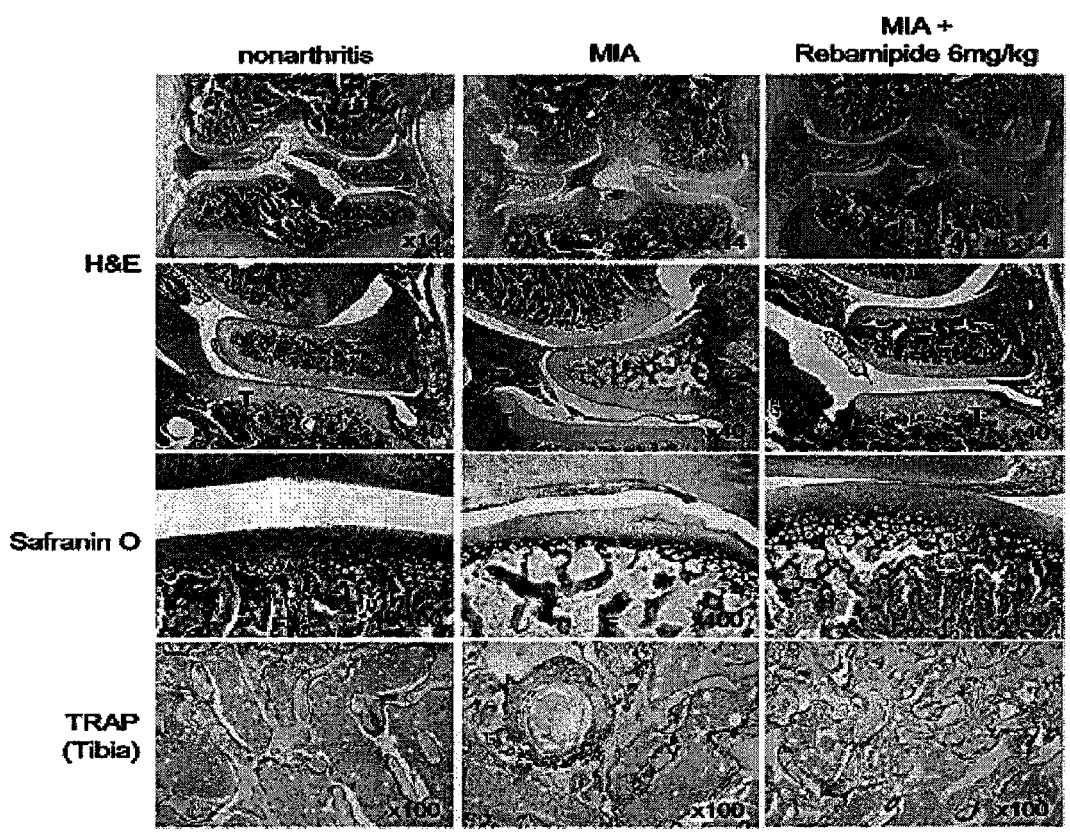
FIG. 2 is the results obtained by histologically analyzing cartilage damages through TRAP, safranin O, and H&E staining.

And, as a result of histological analyses through TRAP, safranin O, and H&E staining, the group not administered with rebamipide showed serious cartilage damages, while the cartilage was remained intact without destruction in the group orally administered with rebamipide (see FIG. 2). That is, as a result of histological analysis through the H&E staining, it was observed that the inflammation in the group orally administered with rebamipide (MIA+Rebamipide) was favorably changed, in comparison with the MIA group. And also, as a result of analysis through the safranin O staining, it was observed in the group orally administered with rebamipide (MIA+Rebamipide) that the surface of the femoral cartilage site was smooth and shown in strong orange-red color, the results of which were similar to the non-arthritis group. In contrast, it was observed in the MIA group that the entire cartilage was weekly stained due to the proteoglycan losses and that the surface thereof became coarse. In addition, as a result of counting the number of osteoclasts in the tibial subchondral bone via TRAP staining, the number of osteoclasts was significantly reduced in the group administered with rebamipide, in comparison with the MIA group.

Figure 3:
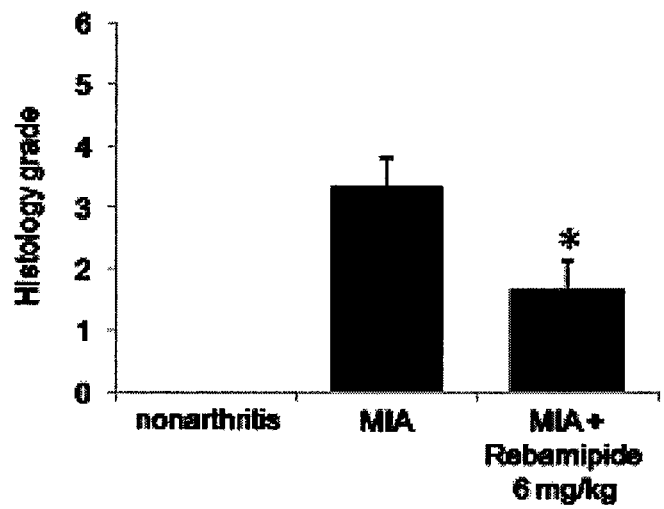
FIG. 3 is a graph illustrating the histology grades calculated from the histological analyses.
Figure 3:
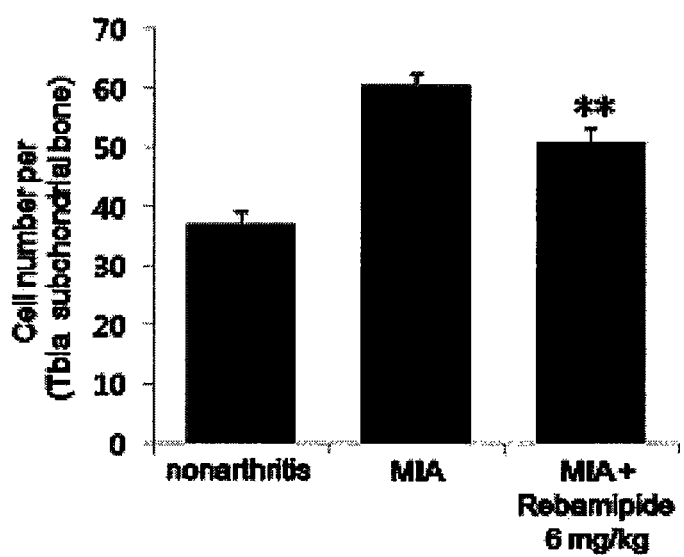

And also, the histology grades were evaluated by scoring based on the standards of Table 1 below; and the results thereof were shown in FIG. 3. As shown in FIG. 3, the MIA group showed reduction in safranin O staining and irregular cartilage surface. However, it was observed in the rebamipide-treated group that the cartilage surface was remained smooth, showing only a little loss of safranin O in the cartilage site.

TABLE 1

| Symptom | Histology grade |
| --- | --- |
| Normal | 1 |
| Slight superficial reduction of safranin O staining | 2 |
| Reduction of safranin O staining and slight surface irregularity | 3 |
| Severe surface irregularity and/or clefts | 4 |
| Full non-calcified cartilage thickness loss | 5 |
| Calcified cartilage loss | 6 |

The above results suggest that rebamipide inhibits cartilage damages, thereby exhibiting an excellent preventive and therapeutic activity against osteoarthritis.

The invention claimed is:

1. A method for treating osteoarthritis in a subject in need thereof, comprising: administering to the subject a pharmaceutical formulation of a tablet or capsule comprising an effective amount of rebamipide or a pharmaceutically acceptable salt thereof, in combination with a pharmaceutically acceptable carrier, wherein rebamipide or a pharmaceutically acceptable salt thereof inhibits cartilage damage, and wherein rebamipide is not co-administered with a NSAID.

2. The method of claim 1, wherein the pharmaceutical formulation comprises an effective amount of rebamipide ranging from 0.5 to 50 mg/kg.

3. The method of claim 2, wherein the amount is ranging from 0.6 to 6 mg/kg.

* * * * *